US00PP34544P2

(12) United States Plant Patent
Roberts et al.

(10) Patent No.: US PP34,544 P2
(45) Date of Patent: Sep. 6, 2022

(54) ***HYDRANGEA* PLANT NAMED 'BAILMACSEVEN'**

(50) Latin Name: *Hydrangea macrophylla*
Varietal Denomination: Bailmacseven

(71) Applicant: Bailey Nurseries Inc., Newport, MN (US)

(72) Inventors: David Jonathan Roberts, Athens, GA (US); Oren McBee, Bishop, GA (US); Justin Schulze, Athens, GA (US)

(73) Assignee: BAILEY NURSERIES INC., Newport, MN (US)

( * ) Notice: Subject to any disclaimer, the term of this patent is extended or adjusted under 35 U.S.C. 154(b) by 0 days.

(21) Appl. No.: 17/527,113

(22) Filed: Nov. 15, 2021

(51) Int. Cl.
*A01H 6/48* (2018.01)
*A01H 5/02* (2018.01)

(52) U.S. Cl.
USPC ..... Plt./250

(58) Field of Classification Search
USPC ..... Plt./250
See application file for complete search history.

*Primary Examiner* — Annette H Para
(74) *Attorney, Agent, or Firm* — Penny J. Aguirre

(57) ABSTRACT

A new cultivar of *Hydrangea macrophylla* plant named 'Bailmacseven' that is characterized by its new foliage growth that is dark purple in color, its dark purple foliage that retains color throughout the summer into fall even in hot summer climates, its inflorescences with sterile sepals that are red-pink in color with creamy white centers (under non-bluing conditions), and its remontant and heavy blooming habit.

2 Drawing Sheets

Botanical classification: *Hydrangea macrophylla.*
Varietal denomination: 'Bailmacseven'.

BACKGROUND OF THE INVENTION

The present invention relates to a new and distinct cultivar of *Hydrangea macrophylla* and will be referred to hereafter by its cultivar name, 'Bailmacseven'. 'Bailmacseven' represents a new mophead type *Hydrangea*, a deciduous shrub grown for use as a landscape plant.

'Bailmacseven' was derived from an ongoing breeding program conducted by the Inventors in Wintersville, Ga. The objectives of the breeding program are to develop new cultivars of *Hydrangea macrophylla* with dark foliage colors and mophead flowerheads that retain coloration all season long.

The Inventors made a controlled cross in summer of 2016 in between unnamed and unpatented proprietary plants from their breeding program accessioned HM16-P4-01 as the female parent and accessioned HM16-R13-02 as the male parent. 'Bailmacseven' was selected in summer of 2018 as a single unique plant amongst the resulting seedlings.

Asexual propagation of the new cultivar was first accomplished by softwood stem cuttings by one of the Inventors in Winterville, Ga. in summer of 2018. Asexual propagation by softwood stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Bailmacseven' as a unique cultivar of *Hydrangea.*

1. 'Bailmacseven' exhibits new foliage growth that is dark purple in color.

2. 'Bailmacseven' exhibits dark purple foliage that retains color throughout the summer into fall even in hot summer climates.
3. 'Bailmacseven' exhibits inflorescences with sterile sepals that are red-pink in color with creamy white centers (under non-bluing conditions).
4. 'Bailmacseven' exhibits heavy blooming habit.

The female parent of 'Bailmacseven' differs from 'Bailmacseven' in having foliage that is dark green in color with purple highlights and inflorescences with sterile sepals that are pink in color. The male parent of 'Bailmacseven' differs from 'Bailmacseven' in having foliage that is dark green in color with purple highlights, a smaller plant size, and lacecap inflorescences with sterile sepals that are pink in color. 'Bailmacseven' can be most closely compared to the *Hydrangea macrophylla* cultivars 'Hokomabebos' (U.S. Plant Pat. No. 34,143) and 'Jon04' (U.S. Plant Pat. No. 30,453). 'Hokomabebos' and 'Jon04' are both similar to 'Bailmacseven' in having mophead type flowers and new growth that is purple in color. 'Hokomabebos' differs from 'Bailmacseven' in having foliage that turns green with purple highlights in summer, inflorescences with sterile sepals that are lighter red-pink in color, and a shorter stem internode length. 'Jon04' differs from 'Bailmacseven' in having foliage that turns to dark green with purple highlights in summer, inflorescences with sterile sepals that are lighter red-pink in color, and a a shorter stem internode length.

BRIEF DESCRIPTION OF THE DRAWINGS

The accompanying color photographs illustrate the overall appearance and distinct characteristics of the new *Hydrangea*. The photographs were taken of a 2-year-old plant as grown in a greenhouse in a 2-gallon container in Cottage Grove, Minn.

Figure 1:
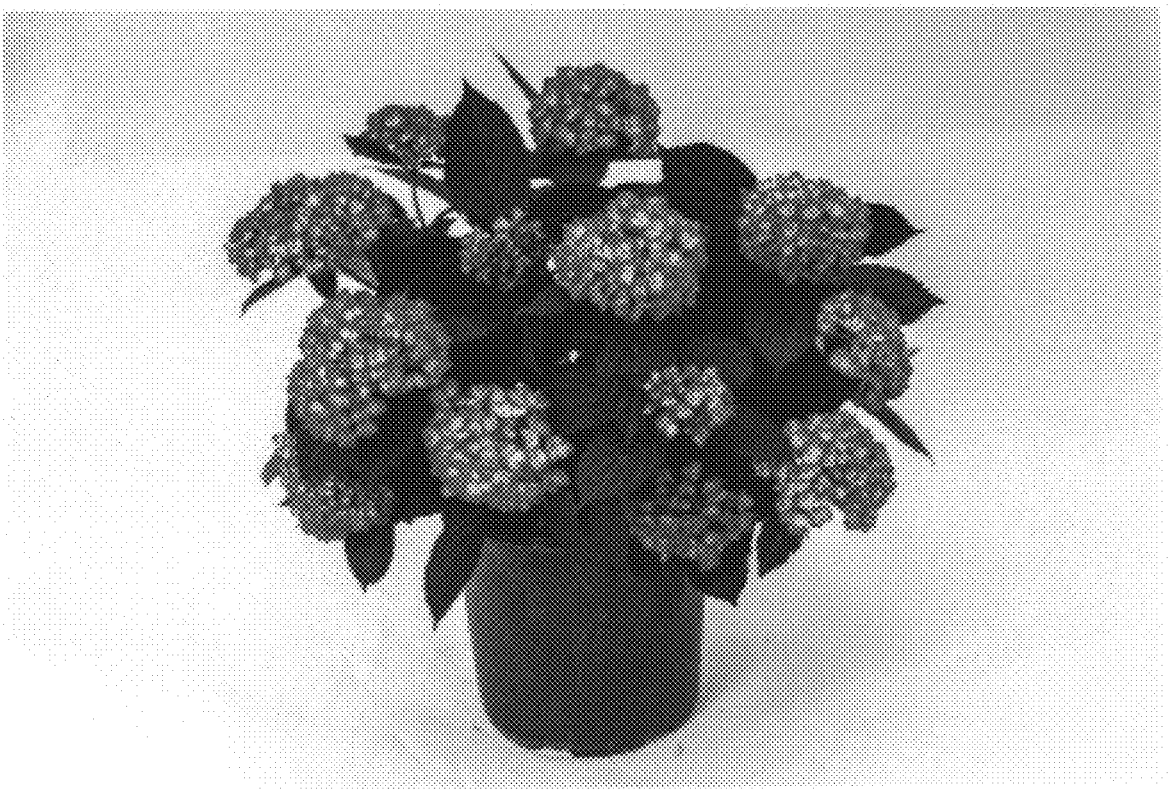
FIG. 1 provides a view of 'Bailmacseven' in bloom.
Figure 2:
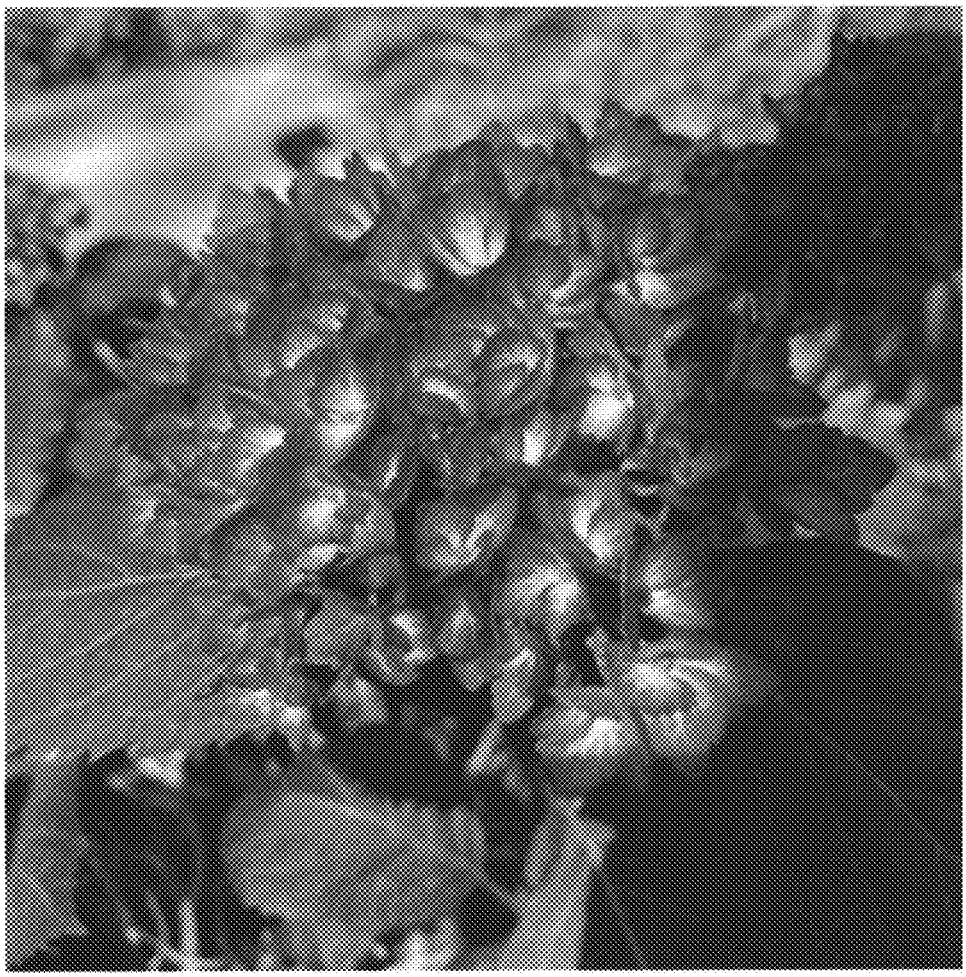

The photograph in FIG. 2 provides a view of an inflorescence of 'Bailmacseven'.

The colors in the photographs may differ slightly from the color values cited in the detailed botanical description, which accurately describe the colors of the new *Hydrangea*.

BOTANICAL DESCRIPTION OF THE PLANT

The following is a detailed description of 2-year-old plants of 'Bailmacseven' as grown outdoors in 2-gallon containers in a greenhouse in Cottage Grove, Minn. The plants were grown under non-blueing conditions. Plants are not being grown under blueing conditions however limited sterile sepal color is provided as recorded from a trial. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period.*—4 weeks in June in Georgia.

*Plant type.*—Deciduous shrub, mophead type *Hydrangea.*

*Plant habit.*—Upright mounded.

*Height and spread.*—Reaches about 46 cm in height and 70 cm in spread as grown in a 2-gallon container, reaches reaching 91 cm to 121 cm in height and width as grown in the landscape in Georgia.

*Hardiness.*—At least in U.S.D.A. Zones 5 to 9.

*Diseases.*—Resistance to powdery mildew (*Podosphaera macularis*) and leafspot (*Cercospora hydrangea*).

*Root description.*—Fine and fibrous, 199B in color.

*Propagation.*—Softwood stem cuttings.

*Growth rate.*—Moderate.

*Root development.*—Softwood cuttings root readily in 6 weeks, rooted cuttings are overwintered and roots will fully develop in a one-quart container by midsummer the following year.

Stem description:

*Stem shape.*—Rounded.

*Stem strength.*—Strong.

*Stem color.*—Young; 145A, mature; 165B.

*Stem size.*—Main branches; average of 19 cm in length, 1 cm in diameter, lateral branches; average of 30 cm in length, 5 mm in diameter.

*Stem surface.*—Younger and mature stems; glabrous, sparsely to moderately lenticellate, lenticles; 5 per $cm^2$, an average of 1.5 mm in length and 0.5 mm in width, N92A in color, old growth at base; bark-like, rugose, slightly fasciated, 165A in color.

*Internode length.*—Average of 8 cm.

*Branching.*—Average of 5 main branches, average of 3 to 5 lateral branches per main branch.

*Stipules.*—Persistent, 2 opposite at base of petioles, stipule bud; is 2 mm in length, 1 mm in width, 79A in color, oblong in shape, acute apex, glossy and glabrous surface.

Foliage description:

*Leaf shape.*—Elliptical.

*Leaf arrangement.*—Opposite.

*Leaf division.*—Simple.

*Leaf base.*—Attenuate.

*Leaf apex.*—Apiculate.

*Leaf margins.*—Serrate.

*Leaf venation.*—Pinnate, upper surface; 142A, lower surface; 142D, flushed with 187A in color.

*Leaf size.*—Average of 14 cm in length and 6.5 cm in width.

*Leaf attachment.*—Petiolate.

*Leaf surface.*—Upper surface; glossy, lower surface; matte.

*Leaf color.*—Young upper surface; N186A, mature upper surface; 202A, young and mature lower surface; a blend of 197A and N189B.

*Petioles.*—An average of 3 cm in length and 3 mm in diameter, young upper surface color 146A, young lower surface color 138A flushed with 183A, mature upper and lower surface 144A, both surfaces glabrous and glossy.

Inflorescence description:

*Inflorescence type.*—Terminal panicle, full rounded mophead in form, comprised of fertile flowers and single sterile flowers.

*Lastingness of inflorescence.*—Persistent for 3 months.

*Inflorescence number.*—One per lateral.

*Inflorescence size.*—Average of 16 cm in height, 17 cm in diameter.

*Flower number.*—Average of 120 sterile flowers and 27 fertile flowers per panicle.

*Flower fragrance.*—Very faint, floral rose fragrance.

*Flower aspect.*—Upright to outward.

*Flower size.*—Sterile flowers; an average of 3.2 cm in diameter, 1 cm in depth, fertile flowers; do not open.

*Flower type.*—Rotate.

*Flower buds.*—Sterile flowers; average of 5 mm in length and 3 mm in diameter, oblong, flattened in shape, color when young; top N79A, mid-section 71A, base 8D, color when mature top 79A, mid-section 62A, base N155C, fertile flowers; average of 3 mm in width and depth, obovate in shape, color when young; a blend of 187A and 46A, color when mature; top N92A, base 62D.

*Peduncles.*—Moderately strong, average of 1.2 cm in length and 2 mm in width, color; a blend of 59A and NN155A, surface is matte, rugose and moderately covered with very minute woolly hairs that matches surface color to NN155A in color.

*Pedicels.*—Moderately strong, average of 8 mm in length and 1 mm in width, color; young pedicels N92A, mature pedicels ranging between 157A and 142B in color, occasionally speckled with 71A in color, surface is matte and moderately covered with very fine woolly hairs that match surface color or NN155A in color.

*Petals.*—Sterile flowers; petals do not fully open, petal spot 1.5 mm in diameter and N92A in color when mature, fertile flowers; petals do not fully open, N92A in color as a flower bud.

*Sepals.*—Sterile flowers; showy, 3 to 4, deltoid to reniform in shape, moderately to strongly overlapping, rotate in arrangement, serrate and crenate margins moderately undulate, apex is very slightly retuse to bluntly pointed, cuneate base, average of 1.7 cm in length and 1.9 cm in width, upper and lower surface glabrous and satiny, color: when opening upper and lower surface; base, center and veins N144A, outside edges 187A to 187B, when fully open upper surface; base, center and veins NN155C, flushed with 145A, outside edges 67A, margins 71A, when fully open lower surface; base NN155C, very lightly flushed with 145A, center 68B to 68C, margins 71A, fertile flowers; do not open, 62A in color and fused into campanula shape as a flower bud, color when fully open upper surface under blueing conditions; a blend of N80B and NN155C, margins N80A, base (centers) NN155C.

Reproductive organs:

*Presence.*—Not observed; fertile flowers drop when mature, gynoecium and androecium not developed.

*Fruit and seed.*—Not observed.

It is claimed:

1. A new and distinct cultivar of *Hydrangea* plant named 'Bailmacseven' substantially as herein illustrated and described.

* * * * *